United States Patent [19]

Narato et al.

[11] 4,008,620
[45] Feb. 22, 1977

[54] SAMPLER FOR ANALYZERS

[75] Inventors: Kiyoshi Narato, Ibaraki; Keizo Ootsuka; Syoichi Sawahata, both of Hitachi, all of Japan

[73] Assignee: Hitachi, Ltd., Japan

[22] Filed: May 5, 1975

[21] Appl. No.: 574,336

[30] Foreign Application Priority Data

May 7, 1974 Japan .............................. 49-49757

[52] U.S. Cl. ......................................... 73/421.5 A
[51] Int. Cl.$^2$ ........................................ G01N 1/24
[58] Field of Search ............. 73/421.5 R, 421.5 A, 73/28

[56] References Cited
UNITED STATES PATENTS

| | | |
|---|---|---|
| 1,100,171 | 6/1914 | Brown ........................... 73/421.5 A |
| 2,682,277 | 6/1954 | Marshall et al. ............... 73/421.5 A |
| 2,691,890 | 10/1954 | Moore, Jr. ...................... 73/421.5 A |
| 2,814,952 | 12/1957 | Pyant, Jr. ...................... 73/421.5 A |
| 3,106,843 | 10/1963 | Luxl .............................. 73/421.5 A |
| 3,289,481 | 12/1966 | Barnes ........................... 73/421.5 A |

*Primary Examiner*—S. Clement Swisher
*Attorney, Agent, or Firm*—Craig & Antonelli

[57] ABSTRACT

An analyzer, and more specifically a sampler for exhaust-gas monitoring and analyzing apparatus, comprising a pipe for introducing clean air into the sampler, a sampling tube for drawing in gasses by suction, and an extracting tube for conducting the gas sample to an analyzer. The sampler is designed so that the admission of clean air thereto creates a sufficient suction effect for drawing in the gasses to be sampled.

6 Claims, 10 Drawing Figures

SAMPLER FOR ANALYZERS

BACKGROUND OF THE INVENTION

1. FIELD OF THE INVENTION

This invention relates to an analyzer, and more specifically to a highly reliable sampler for exhaust gases.

It is known that the dilution of the gas sample is essential for the analysis of exhaust gases, such as flue gases with high dust concentrations or highly concentrated sulfurous acid gases, by means of an aerosol monitoring instruments, flame intensity type $SO_2$ analyzer or the like which can analyze only the gases containing smoke dusts (particulates) or $SO_2$ in low concentrations.

Also, when measuring the dust content of flue gases, it is imperative to sample the gases by so-called synchronized suction, or at the rate of suction in the inlet of the nozzle made equal to the flow velocity of the gases.

The present invention is concerned with an exhaust-gas sampler which can easily accomplish the dilution and synchronized suction to meet the foregoing requirements.

2. DESCRIPTION OF THE PRIOR ART

Prior art arrangements will now be described, by way of exemplification, in connection with aerosol monitoring.

As is known in the art, aerosol is a system consisting of a gas in which fine solid or liquid particles are suspended. Attempts have recently been made to utilize aerosol monitoring instruments of the light scattering type for continuous automatic measurement of the dust content of flue gases. The measuring instruments for this purpose are called stack dust monitors of the light scattering type. Generally, the dust content of flue gases is over the measurable range of the light scattered type stack dust monitor, and therefore the sample of the gas drawn in must be diluted with from 10 to 1000 times by volume of dry clean air. At the same time, th temperature and water content must be decreased. The dulution is done by either of two different means, closed and open types.

The dilution means of the closed type samples a part of flue gases, mixes it with clean (diluting) air being recycled (by a recycling system provided independently of the extracting system), and then extracts the gaseous mixture for an aerosol monitoring instrument. Because of the construction described, the closed type requires, in addition to the filter or filters and the pump for obtaining the clean air, a dehumidifier for removing the drain water as the condensate of the moisture content of flue gases collected gradually as a result of recycling. Inevitably, the closed type apparatus has to be large and heavy.

On the other hand, the open type is free of the system for recycling clean air that is needed by the closed type. It thus need no such means for removing mists and the like from flue gases as is required by the closed type. Naturally, the open type may be smaller in size and lighter in weight than the closed type.

The conventional sampling method of the open type nevertheless has drawbacks in that the variation of the flue static pressure is accompanied by the corresponding variation of the quantity of flue gases being drawn in from the flue to the extractor because the mixed gas after the static pressure variation is directly extracted for the aerosol monitoring instrument and, consequently, the dilution multiple is not kept constant and an error in measurement will result.

Another disadvantage of the conventional method arises from the fact that the flow rate of the sample being extracted for analysis by the aerosol monitoring instrument is constant. If the flow rate is to exactly correspond to a changed flow velocity of exhaust gases, the suction nozzle of the sampling tube must be modified in diameter to maintain synchronized suction. This is impractical and, therefore, control of synchronized suction is next to impossible.

SUMMARY OF THE INVENTION

The present invention has for its object to eliminate the afore-described disadvantages of the prior art instruments and provide a sampler for analyzers which can effect dilution and synchronized suction with a constant dilution multiple and a high degree of efficiency.

The invention is characterized in that, in an analyzer using the open type sampling method, clean air is introduced into the sampler and, by dint of the injection effect, ejection effect or the like thereby created, the gases to be examined are drawn into the sampler by suction.

The manner in which the foregoing and other objects of this invention are accomplished will become more apparent from the following description, taken in connection with the accompanying drawings showing embodiments thereof.

DETAILED DESCRIPTION

Figure 1:
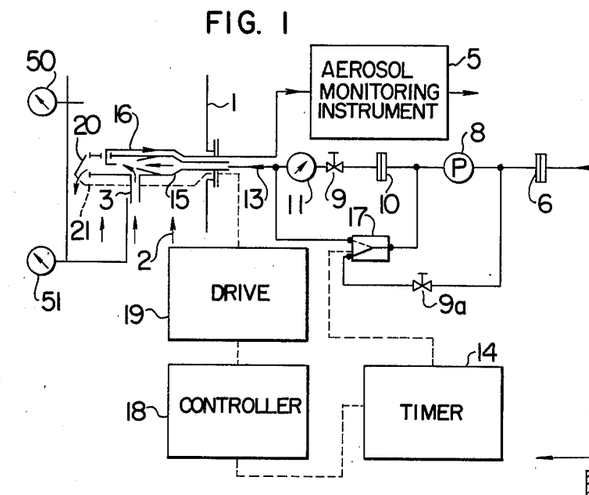
FIG. 1 is a schematic view of an embodiment, illustrating the principles of the invention.

Referring now to FIG. 1, there is shown an arrangement according to the invention for measuring the concentration of smoke dust in stack emission by drawing off a part of exhaust gases from a flue 1 into a sampling tube 3 and then extracting the sample by means to be described later into a aerosol monitoring instrument 5. Air from the atmosphere is drawn in by a pump 8, passed through a prefilter 6 and a main filter 10, and then is introduced as clean (diluting) air into a sampler 15. The quantity of air to be supplied in this way is regulated by sending a part of the air from the exit of the pump 8 via a three-way solenoid valve 17 back to the entrance of the same pump, the amount of the recycling air being controlled with two valves 9, 9a. As the clean air is admitted at a predetermined rate thereto, the sampler 15, which is built as an injector inside, produces a sucking force corresponding to the quantity of clean air being introduced in its sampling tube 3 for drawing in exhaust gases 2 by suction from a flue 1, in the arrangement of the embodiment shown. The sampling tube sucks a quantity of the flue gases 2 in proportion to the quantity of clean air $A_{cq}$. The flue gases introduced are mixed with the clean air and are thereby diluted in the sampler 15. The aerosol monitoring instrument 5 has a built-in pump (not shown) with which to draw in the diluted gases with a low aerosol concentration through an extraction tube 16 at a constant rate, e.g., at 100 l/hr, so that the gases are conducted to an optical sensor or the instrument 5 for the measurement of the smoke dust concentration. When the aerosol monitoring instrument 5 is of the type equipped with an optical sensor, the scattered light method is employed. The gas-extracting opening of the sampling tube 3 that also serves as the measuring mouth of a smoke-dust measuring instrument is usually not less than 4 mm in diameter. Therefore, there are apparently few possibilities of clogging of the extracting opening or other part of the sampling tube due, for example, to dust deposition during the course of continuous operation. The tube must, however, be purged for extended life. For this reason the sampler 15 is provided with purging means now to be described. As described, a part of clean air is normally recycled from the exit of the pump 8 to the entrance of the pump via the three-way solenoid valve 17. A timer 14, connected to the solenoid valve 17, switches the circuit including the valve after the lapse of a predetermined period of time, e.g., about 30 to 60 minutes, so that the recycling circuit leading to the entrance of the pump is shut off and a circuit connecting to the outlet of a flow meter 11 is made, instead. Consequently, the total quantity of air taken in from the atmosphere is introduced into the sampler 15. The timer 14 is also connected to a controller 18 so that the actuation of the timer starts a drive 19 operatively connected to the controller, and thereby closes a damper 20 through a linkage 21. With the damper 20 closed, the sampler 15 causes the trapped clean air to jet out through the sampling tube 3 into the flue, thus purging the sampling tube 3 of any deposit on its inner surrounding wall.

Figure 2:
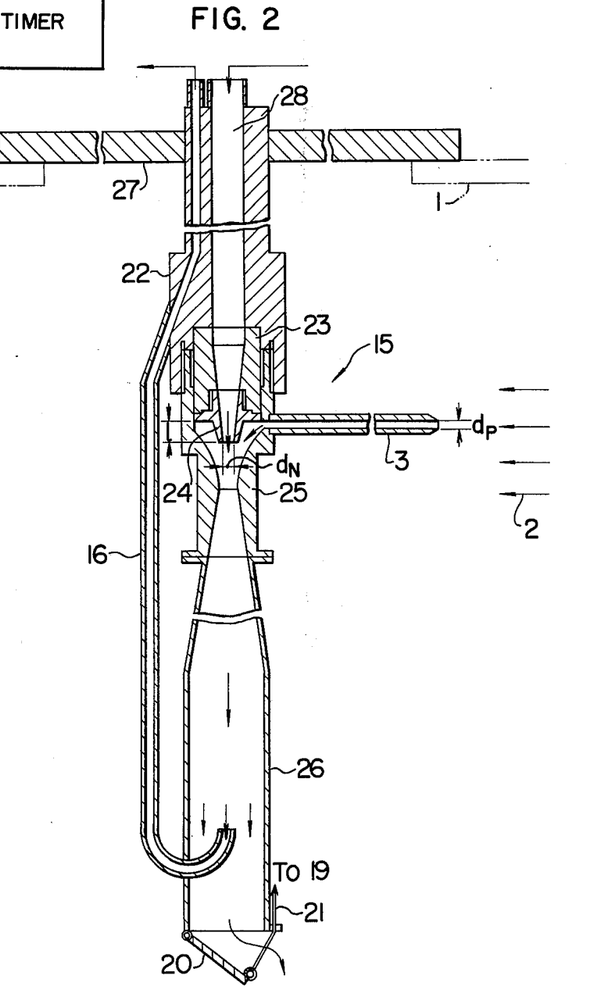
FIG. 2 is a sectional view of a sampler as used in the arrangement of FIG. 1, showing the internal construction.

FIG. 2 is a sectional view of the sampler 15 shown in FIG. 1 in accordance with the invention. Throughout these figures like numerals denote like parts. The construction and function of the sampler will now be described in detail. Here are shown a clean air pipe 22, a nozzle support 23, a nozzle 24, and a reducer 25 which is a constriction in which the flue gases 2 drawn in through the sampling tube 3 are mixed and diluted with clean air admitted through a clean air entrance 28 and the pressure is recovered. The tube 16 for extracting diluted aerosols is built in a duct 26. The sampler 15, comprising the sampling tube 3, damper 20, extracting tube 16, clean air pipe 22, nozzle support 23, nozzle 24, reducer 25, and duct 26, is held in place by a flange 27.

The operation of the sampler 15 with the construction above described will now be explained. Clean air is introduced from the entrance 28 into the nozzle 24. As the clean air is issued from the nozzle 24, a negative pressure is produced in the portion of the sampling tube 3 adjacent to the nozzle 24, and thereby a part of the exhaust gases 2 from the flue 1 is drawn in through the sampling tube. In other words, the injection effect thus achieved permits the sampling of the flue gases 2. The reducer 25, designed to increase the force with which the flue gases 2 are drawn in by suction and also to rectify the gas stream and allow it to recover the original pressure, now mixes and dilutes the gases with clean air.

Figure 3:
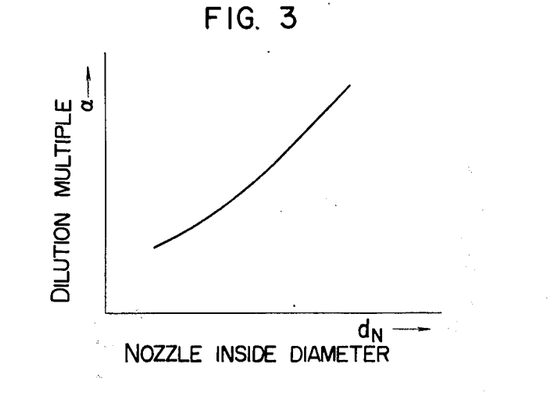
FIG. 3 is a graph showing the relation between the inside diameter of the nozzle and the dilution multiple used by the sampler of FIG. 2.

The relationship between the quantity of clean air $A_{cq}$ and the quantity of aerosols to be measured q depends largely on te inside diameter $d_N$ and length $l$ of the nozzle 24 and on the inside diameter $d_p$ of the sampling tube 3. Therefore, if the flue gases 2 or the aerosols are to be diluted so that the particulates in the diluted aerosols extracted for the aerosol monitoring instrument 5 fall within the measurable range of the instrument, it is only necessary to change the inside diameter $d_N$ of the nozzle, provided that the length $l$ of the nozzle 24 and the inside diameter $d_P$ of the sampling tube 3 remain unchanged. In this way the dilution multiple $\alpha [= (1 + A_{cq})/q]$ may be varied according to the particulate concentration in the aerosols to be examined. This relationship is graphically represented in FIG. 3.

Following the dilution in the reducer 25, the aerosols are conducted by the duct 26 and through the extracting tube 16 inserted into the duct 26, and a part of the diluted aerosols is drawn into the aerosol monitoring instrument 5 by means of the pump (not shown) incorporated therein.

Figure 4:
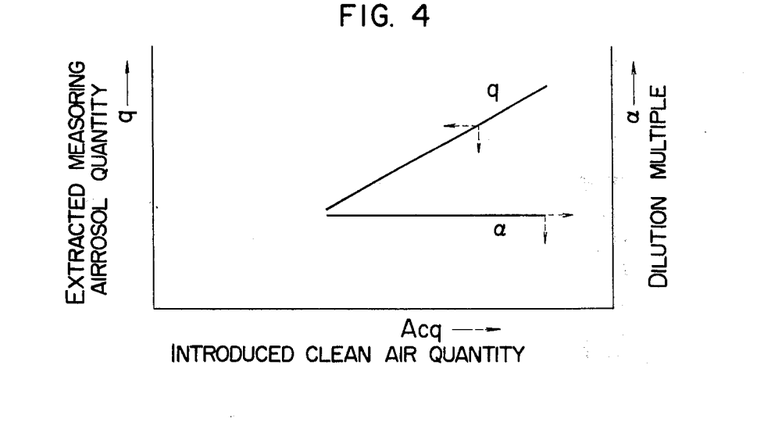
FIG. 4 is a graph showing the relations among the quantity of clean air introduced into the sampler of FIG. 2, the quantity of aerosols drawn into the instrument for analysis, and the dilution multiple employed.
Figure 5:
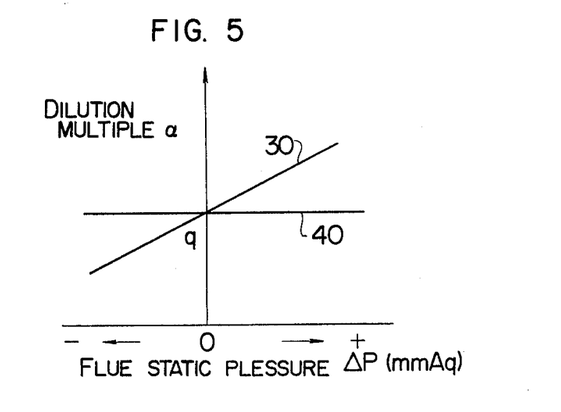
FIG. 5 is a graph showing the relation between the flue static pressure and the dilution multiple as used in FIG. 2.

In FIG. 4 are plotted the relations among the quantity of clean air $A_{cq}$ introduced into the sampler 15, the quantity of aerosols q drawn in through the sampling tube 3 for analysis, and the dilution multiple $\alpha$ employed. When the sampler of the structure shown in FIG. 2 in accordance with the invention is used, the aerosol quantity q to be drawn in through the sampling tube 3 can be varied by merely changing the quantity of clean air $A_{cq}$ to be admitted to the tube. In this case, because of the linear relationship between the variables $A_{cq}$ and $9$, the dilution multiple $\alpha$ can be kept constant independently of the quantity $A_{cq}$. If the flow velocity of exhaust gases in the flue fluctuates because of variation in the stack emission, sampling can be adjusted accordingly through the regulation of clean air introduction. This precludes any error in suction.

FIG. 5 illustrates the relation between the flue static pressure variation $\Delta P$ ($mmAq$) and the dilution multiple $\alpha$. According to the invention, the static pressure of the aerosols to be analyzed is made equal to that of the aerosols after dilution, and the pressure of clean air to be issued from the orifice of the nozzle 24 shown in FIG. 2 is higher than the range of static pressure variation in the flue 1. Consequently, regardless of the flue static pressure variation, the dilution multiple $\alpha$ remains constant as represented by the straight line 40 in the graph. For reference purpose the characteristic of a conventional apparatus is given as line 30, which indicates that the dilution multiple $\alpha$ varies with the flue static pressure variation $\Delta P$. Defenite dimension and operating conditions of the sampler 15 that satisfy the foregoing conditions are, for example, $d_N = 6$ mm, $l = 10$ mm, $A_{cq} = 4000 - 9000$ $l/hr$, and $d_P = 4$ mm. In this case, $\alpha = 10$.

As described above, in accordance with the present invention, the injection effect attained with the introduction of clean air into the sampler is utilized to draw a sample of gas by suction into the same vessel. The invention thus provides a high-performance sampler for analyzers which dispenses with a dehumidifier, requires no positive limitation to the leak of the pump that introduces clean air into the instrument, and is small and lightweight, operable with a constant dilution multiple regardless of variation in the quantity of clean air being introduced. Another outstanding feature of the high-performance sampler for analyzers that is provided by the invention is that, because the sampler is installed in the atmosphere of the gases to be analyzed in such a manner that the static pressure of the atmosphere of the gases to be analyzed is equal to that of the sample diluted, the dilution multiple is kept constant regardless of any variation in the static pressure of the gas atmosphere.

Although the embodiment shown in FIG. 1 is intended for the illustration of the sampler according to the invention as used with an aerosol monitoring instrument, it should be understood that the invention is not limited thereto but is applicable to other high-sensitivity analyzers, such as flame intensity type $SO_2$ analyzers, which must dilute the samples of gaseous materials prior to analysis. Also, while the atmosphere of gases to be analyzed have been limited in the foregoing description to flue gases, other atmospheres, such as in tanks or other vessels, may, of course, be handled as well. Further, the clean air used in diluting the sampler may be replaced by other clean gases, such as pure nitrogen.

When the dilution multiple is to be changed, it is simply necessary to change the inside diameter of the nozzle 24 shown in FIG. 2. Also, it is possible to increase the dilution multiple by providing a diluting system consisting of a plurality of samplers having the nozzles 24 each designed for a given dilution multiple and connected in cascade fashion to the reducer 25.

In another embodiment of the invention, an ejection effect is utilized as means for sampling exhaust gases. In this arrangement, a part of gases drawn into the suction pipe by an ejector is conducted to a monitoring instrument, and the rest of the gases and a gas led into the ejector are altogether removed from the sampler by way of an eduction passage or duct. The sampling nozzle and the eduction duct, both of which are communicated with the suction pipe, are kept in atmospheres under the same pressure, and means is provided for controlling the flow rate of the gas being admitted to the ejector.

The embodiment of the invention which thus depends on the ejection effect for the suction sampling will be more fully described below with reference to FIGS. 6 through 10.

Figure 6:
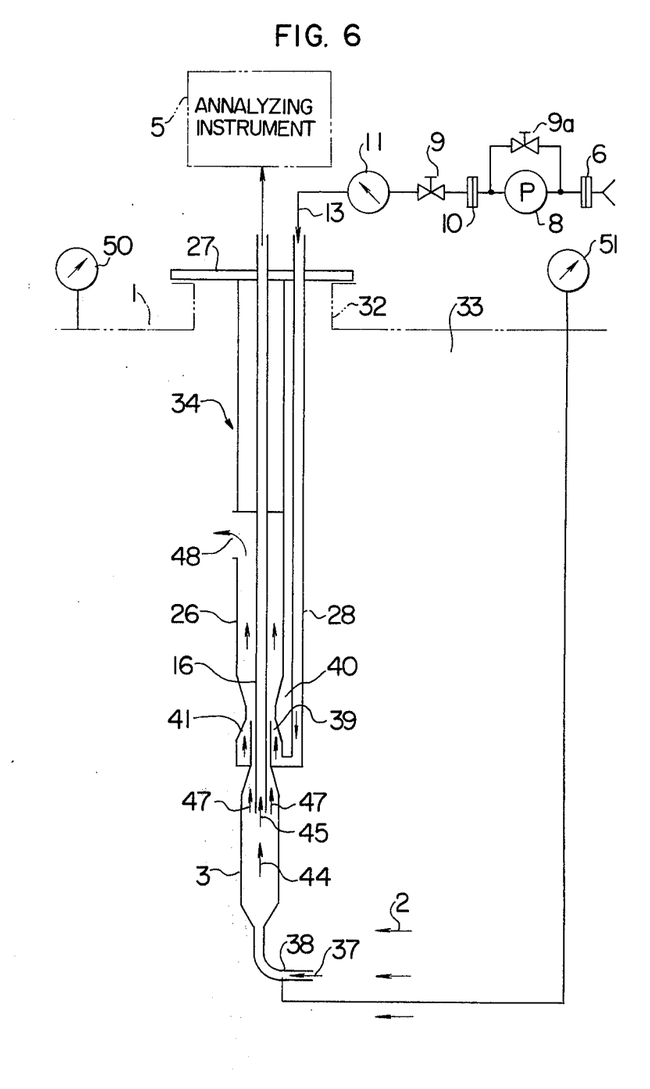
FIG. 6 is a schematic view of another embodiment of the invention.
Figure 7:
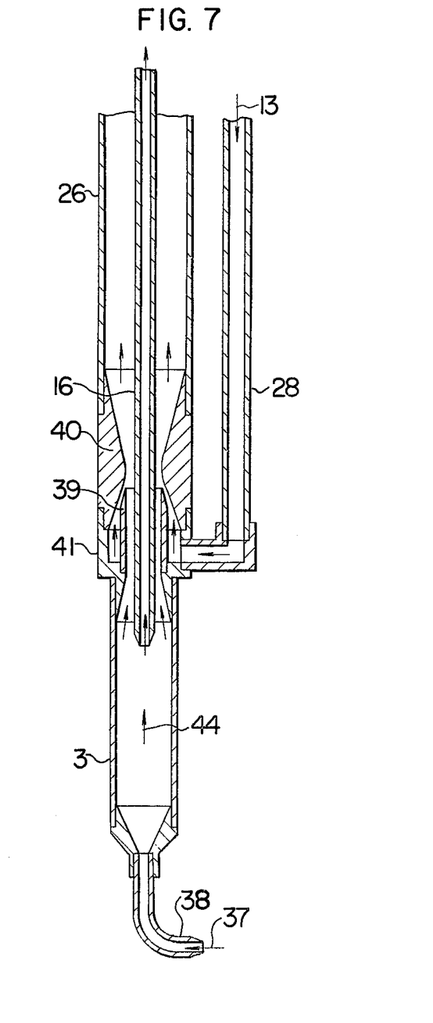
FIG. 7 is a sectional view of the sampling probe, the key part of the arrangment shown in FIG. 6.

FIG. 6 schematically shows the construction of the sampler according to the invention, and FIG. 7 is a sectional view of the sampling probe, the essential component of the arrangement shown in FIG. 6. Throughout these figures like numerals designate like parts. Turning to FIG. 6, the sampling probe generally indicated at 34 is inserted into the space 33 of a flue 1 through a measuring hole 32 formed in the wall of the flue, and is suspended by a flange 27 secured to the hole. The sampling prove 34 comprises: an ejector 41 which consists of an air supply pipe 28 through which air 13 is supplied, and ejector nozzle 39, and a throat 40; a suction pipe 3 connected at one end to the ejector nozzle 39 and provided with a sampling nozzle 38 at the free end for drawing in exhaust gases 37 by suction; an extracting tube 16 for conducting a part of exhaust gases taken in through the sampling nozzle 38, from the inside of the sampling pipe to an analyzing instrument 5; and an eduction pipe or duct 26 for removing the rest of exhaust gases drawn in through the sampling nozzle 38 and the air from the ejector 41.

Figure 8:
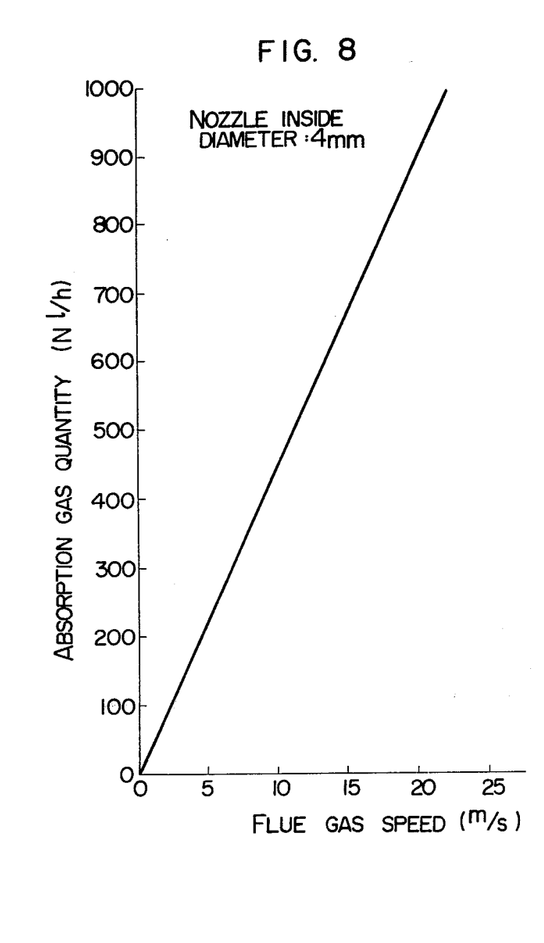
FIG. 8 is a graph showing the relation between the flue gas speed and the quantity of gases drawn in during sampling at a constant suction speed.

The operation of the arrangement will now be explained. Air 13 is supplied at a high speed through the pump 8, flow meter 11, and air supply pipe 28 to the ejector 41. As it passes between the throat 40 and the ejector nozzle 39, the air gives birth to an ejection effect, which in turn produces a negative pressure in the opening of the ejector nozzle 39 and thereby draws in the exhaust gases 37 from the flue through the sampling nozzle 38. A part of the exhaust gases introduced is conducted by suction through the extracting tube 16 to the instrument 5 by means of a built-in pump (not shown) of the instrument. When measuring the smoke dust concentration of exhaust gases 37, it is necessary to sample the gases 37 with the same dust concentration as in the flue, and therefore sampling by synchronized suction is important. For this purpose the flow speed of the exhaust gases 37 being drawn into the sampling nozzle 38 through its opening must be equal to the flow speed of the gases in the flue 1. Meanwhile, the nozzle 38 is usually 4 mm or more in inside diameter. If the diameter is 4 mm, a linear relationship will hold, as shown in FIG. 8, between the flow speed of the flue gases 2 and the quantity of gases drawn in by suction, at the time when the flow speed of the exhaust gas stream 2 equals that of the gases 37 at the mouth of the nozzle 38. Since the flue gas speed usually is not less than 5 meters per second, the quantity of the gases drawn in at that speed will be approximately 200 N$l/h$ or upwards. However, the quantity of the gas sample actually required by the measuring instrument 5 is only about 100 N$l/h$. For this reason the total quantity of the gas sample taken in through the nozzle 38 cannot be directed to the instrument; only a part has to be extracted for analysis.

In accordance with the present invention, an ejection effect is utilized to draw in exhaust gases by suction, and a sample of gases from the flue 1 is introduced into the suction pipe 3 via the nozzle 38 of a given diameter of 4 mm or more, and a part of the gas sample is directly conducted without dilution into the measuring instrument 5 through the extracting tube 16 inserted into the suction pipe. In order to equalize the flow speed of the gases being drawn in through the nozzle 38 to that of the gases in the flue, the pump 8 is associated with a bypass valve 9$a$ and a valve 9 so that the flow rate of the air 13 being supplied to the ejector 41 can be adjusted through the manipulation of the valves 9$a$, 9. As a part 45 of the gas sample 44 introduced into the suction pipe 3 is further drawn off into the measuring instrument 5 through the extracting tube 16, sampling by synchronized suction is again required, that is, the flow speed of the gas sample 44 in the suction pipe 3 must be equal to that of the gases 45 at the inlet opening of the extracting tube 16. When the rate at which the gas sample is supplied to the instrument 5 is variable, the rate of gas supply is so chosen as to be equal to the flow rate of the gas sample in the suction pipe.

Usually, however, the rate of gas supply is kept constant, and the suction pipe of a sufficiently large inside diameter is used to keep the flow speed of the gas sample 44 low, so that the error due to unsynchronized suction may be neglected. When the gas quantity being supplied to the measuring instrument 5 is constant, the gas speed in the suction pipe 3 is equal only at one point to that in the inlet opening of the extracting tube 16. If the flow speed of the gas sample 44 in the suction pipe 3 is low, the error in sampling of smoke dust will decrease accordingly even though the sampling is done by unsynchronized suction, and therefore the inside diameter of the suction pipe 3 may be increased until the gas speed drops to the level where the deposition of smoke dust by setting down can be disregarded.

While a part of the gas sample 4 taken in through the suction pipe is conducted through the extracting tube 16 to the measuring instrument 5, the rest 47 of the gases is discharged, together with the air 13 supplied to the ejector 41, to the flue 1 through the duct 26 and its exit 48. Because no flue gas other than the sample is released out of the flue, there is practically no disposal problem after the sampling. An additional advantage is that, since the inlet of the sampling nozzle 38 and the exit 48 of the duct 26 are open in the same atmosphere at the same pressure, synchronized suction is made possible without being influenced in any way by the static pressure in the flue. This concept is applicable as well to the embodiment of the injection type already described in conjunction with FIG. 1.

Figure 9:
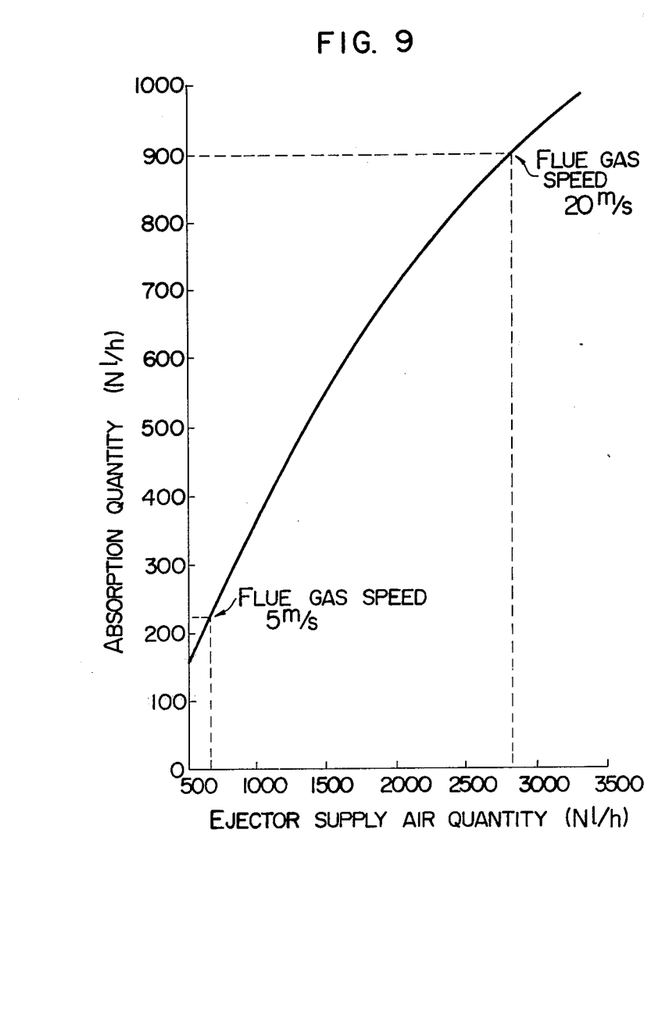
FIG. 9 is a graph showing the relation between the quantity of air supplied to the ejector and the quantity of gases drawn in by suction.

FIG. 9 is a graph showing the relation between the quantity of air supply to the ejector and the quantity of flue gases taken in for sampling. It will be seen from FIGS. 8 and 9 how much air should be supplied to the ejector in order to equalize the speed of gases being drawn in through the sampling nozzle to that of the gases flowing in the flue, when the flue gas speed has changed. If such is the case, it is merely necessary to manipulate the bypass valve 9a and the like while watching the flow meter 11 until the equalization in flow rates is attained. The bypass valve may be operated by hand or automatically through linkage to means for sensing the flow speed of the gas stream 2 in the flue.

With the sampler shown in FIGS. 6 and 7 which relies upon an ejection effect for the sampling action, it is also possible to locate the free end of the extracting tube 16 that conducts the sample 45 for analysis to the analyzing instrument 5, rearwardly of the ejector 41 (toward the flange 27), and thereby accomplish the dilution and suction of a part of the gaseous mixture, which was obtained by mixing and diluting the exhaust gases 37 drawn in by the ejection effect with the air 13 supplied to the ejector 41, for introduction into the analyzing instrument 5 through the extracting tube 16. In this manner the same result is obtained as with the sampler of FIG. 1 that makes use of the injection effect for the sampling purpose. Another feature of this second embodiment of the invention is that the dilution multiple can be kept unchanged in disregard of any variation in the quantity of air 13 being supplied to the sampler.

Figure 10:
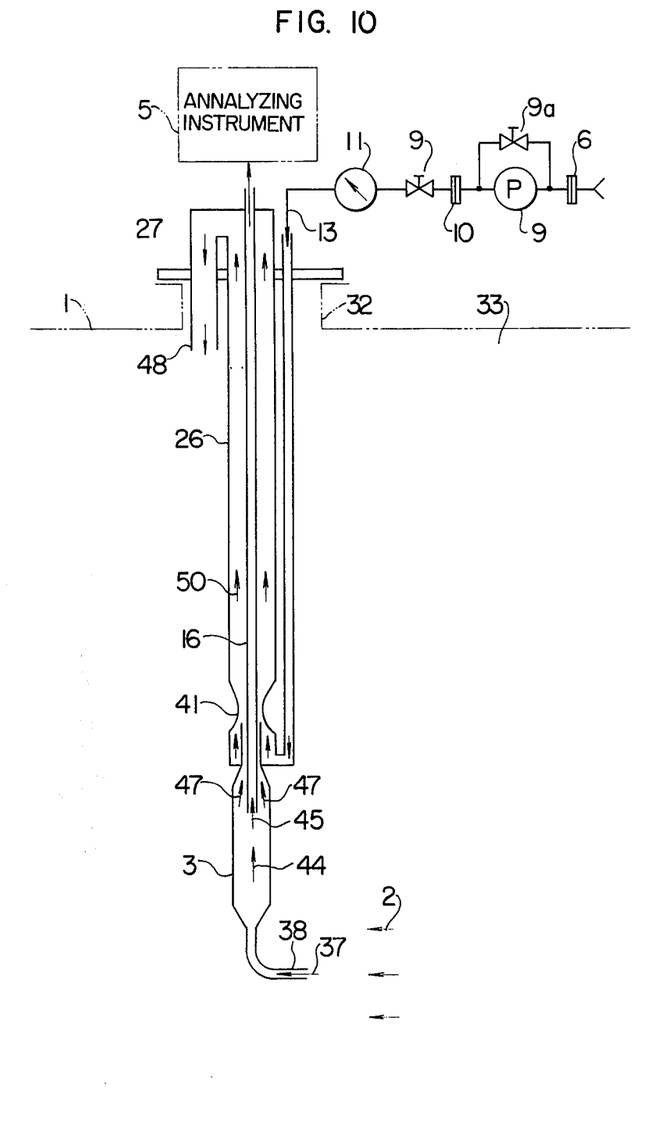
FIG. 10 is a schematic view of still another sampler embodying the invention.

FIG. 10 shows still another embodiment of the invention. Throughout FIGS. 1, 6, and 10 like numerals indicate like or corresponding parts. In this embodiment the eduction pipe or duct 26 is once extended through the flange 27 to the outside of the flue 1 and then bent back to open 48 in the flue. The structure renders it possible to utilize the heat of the exhaust gases 50 in heating the extracting tube 16. It thus prevents cooling of the extracting tube 16 outside of the flange 27 and the flue 1, and avoids dew condensation of the moisture content of the gas sample 45.

As stated above, the sampler of the invention is outstandingly advantageous in that it permits the operation from the outside to effect sampling by synchronized suction through an increase in the inside diameter of the sampling nozzle. In addition, like the embodiment shown in FIG. 1, those of FIGS. 6 and 10 may have purging means, too.

The method of operating the embodiments of FIGS. 1 and 6 from the outside for their sampling by synchronized suction is to manipulate the valve 9a and/or the valve 9 until the reading of the pressure gauge 50 for the flue gases in the flue and the reading of the pressure gauge 51 for the flue gases entering the sampling tube 3 become equal, so that the flue gas pressure is equalized to the gas pressure in the sampling tube. In this way synchronized suction is carried out.

For dust monitors the synchronized suction is essential because the monitors, which measure the dust contents of flue gases, tend to give higher or lower readings than the actual values of dust concentrations unless the gases are sampled by syychronized suction.

For the instruments other than dust monitors, which merely measure gas compositions, the means for realizing the synchronized suction is not always required.

Although the present invention has been described in connection with preferred embodiments thereof as divided into two types, injection and ejection types, the both are common in that they take in sample gases for the analyzing instrument by taking advantage of the phenomenon of suction by the diluting gas.

As has been described above, this invention provides a sampler for analyzing equipment having a highly efficient diluter operable with a constant dilution multiple.

What is claimed is:

1. A sampler for analyzers comprising a clean-gas supply pipe provided with a nozzle tip which may or may not be interchangeable, a sampling tube for drawing in a sample for analysis, an extracting tube for conducting the sample after dilution to an analyzing instrument, said sample being admitted to the sampler as a result of the suction created by the clean gas during its introduction into the same vessel, said sample then being diluted with the clean gas and led to the analyzer via the extracting tube, and which also comprises a suction pipe in which the free end of the extracting tube for conducting the sample to the analyzer is extended to an intermediate point of the pipe, and a sampling nozzle attached to the free end of the suction pipe.

2. A sampler for analyzers comprising a clean-gas supply pipe provided with a nozzle tip which may or may not be interchangeable, a sampling tube for drawing in a sample for analysis, an extracting tube for conducting the sample after dilution to an analyzing instrument, said sample being admitted to the sampler as a result of the suction created by the clean gas during its introduction into the same vessel, said sample then being diluted with the clean gas and led to the analyzer via the extracting tube, and which also comprises means for purging the sampling tube.

3. A sampler for analyzers comprising a clean-gas supply pipe provided with a nozzle tip which may or may not be interchangeable, a sampling tube for drawing in a sample for analysis, an extracting tube for conducting the sample to an analyzing instrument, said sample being admitted to the sampler as a result of an injection effect produced by clean gas during its introduction into the same vessel, said sample then being diluted with the clean gas and led to the analyzer via the extracting tube, and which also comprises a suction pipe in which the free end of the extracting tube for conducting the diluted sample to the analyzer is extended to an intermediate point of the pipe, and a sampling nozzle attached to the free end of the suction pipe.

4. A sampler for analyzers comprising a clean-gas supply pipe provided with a nozzle tip which may or may not be interchangeable, a sampling tube for drawing in a sample for analysis, an extracting tube for conducting the sample to an analyzing instrument, said sample being admitted to the sampler as a result of an injection effect produced by clean gas during its introduction into the same vessel, said sample then being diluted with the clean gas and led to the analyzer via the extracting tube, and which also comprises means for purging the sampling tube.

5. A sampler for analyzers comprising a clean-gas supply pipe provided with a nozzle tip which may or may not be interchangeable, a sampling tube for drawing in a sample for analysis, and an extracting tube for conducting the sample to an analyzing instrument, said sample being extracted into the sampler as a result of an ejection effect produced by the clean gas during its introduction into the same vessel, said sample then being diluted with the clean gas and led to the analyzer via the extracting tube, and which also comprises a suction pipe in which the free end of the extracting tube for conducting the diluted sample to the analyzer is extended to an intermediate point of the pipe, and a sampling nozzle attached to the free end of the suction pipe.

6. A sampler for analyzers comprising a clean-gas supply pipe provided with a nozzle tip which may or may not be inerchangeable, a sampling tube for drawing in a sample for analysis, and an extracting tube for conducting the sample to an analyzing instrument, said sample being extracted into the sampler as a result of an ejection effect produced by the clean gas during its introduction into the same vessel, said sample then being diluted with the clean gas and led to the analyzer via the extracting tube, and which also comprises means for purging the sampling tube.

* * * * *